United States Patent
Mir

(10) Patent No.: US 11,001,541 B2
(45) Date of Patent: May 11, 2021

(54) METHODS FOR GENERATING PURIFIED CYCLOPROPENES

(71) Applicant: Nazir Mir, Somerset, NJ (US)

(72) Inventor: Nazir Mir, Somerset, NJ (US)

( * ) Notice: Subject to any disclaimer, the term of this patent is extended or adjusted under 35 U.S.C. 154(b) by 0 days.

(21) Appl. No.: 16/540,001

(22) Filed: Aug. 13, 2019

(65) Prior Publication Data

US 2021/0047247 A1 Feb. 18, 2021

(51) Int. Cl.
*C07C 1/32* (2006.01)
*B01L 3/10* (2006.01)
*B01D 53/14* (2006.01)
*C07C 7/11* (2006.01)
*C07C 7/00* (2006.01)
*C07C 7/04* (2006.01)

(52) U.S. Cl.
CPC .......... *C07C 1/328* (2013.01); *B01D 53/1418* (2013.01); *B01L 3/10* (2013.01); *C07C 7/005* (2013.01); *C07C 7/04* (2013.01); *C07C 7/11* (2013.01); *C07C 2601/02* (2017.05)

(58) Field of Classification Search
CPC .......... C07C 1/328; C07C 7/005; C07C 7/04; C07C 7/11; C07C 2601/02; B01D 53/1418; B01D 3/10
See application file for complete search history.

(56) References Cited

U.S. PATENT DOCUMENTS 6,953,540 B2 * 10/2005 Chong .................... B01J 13/02
264/4.1

OTHER PUBLICATIONS

Neoh et al. ("Kinetics of Molecular Encapsulation of 1-Methylcyclopropene into α-Cyclodextrin" J. Agric. Food Chem. 2007, 55, 26, 11020-11026) (Year: 2007).*

Chen ("Development of liquid 1-methylcyclopropene delivery formulations for modifying ethylene response of fresh produce" https://doi.org/doi:10.7282/T3571DZZ, Oct. 2015) (Year: 2015).*

* cited by examiner

*Primary Examiner* — Youngsul Jeong
*Assistant Examiner* — Jason Y Chong
(74) *Attorney, Agent, or Firm* — Rueppell Consulting; Chris Rueppell

(57) ABSTRACT

The present invention relates to methods of preparing purified cyclopropylene (1-methylcyclopropylene) gas employing one or more non-reactive purification processes to purify substances including, without limitation, cyclopropene (1-methylcyclopropylene) gas and/or lithio-cyclopropene.

20 Claims, 8 Drawing Sheets

METHODS FOR GENERATING PURIFIED CYCLOPROPENES

BACKGROUND

Current understanding based on more recent investigations into cyclopropene compounds have revealed various applications and uses of these compounds in the chemical industry. In particular, 1-methylcyclopropene (1-MCP), and its related analogs, are understood as highly effective in controlling and/or inhibiting the adverse effects of ethylene in plants thereby promoting delayed ripening and senescence (see Blankenship & Dole, 2003) (see also U.S. Pat. No. 5,518,988). As such, commercially (cost) efficient and effective generation, storage and use of these compounds, such as 1-MCP, have become significantly important considerations in the industry.

Synthesis of cyclopropene compounds usually involves reaction between an allylic halide such as methallyl chloride or 3-chloro-2-methylpropene (3-CMP), and a strong base such as lithium diisopropylamide (LDA), phenyllithium and/or sodium amide (Fisher & Applequist, 1965; Magid, Clarke, & Duncan, 1971). In this synthesis reaction, the halogen group in the allylic halide undergoes an elimination reaction and the remaining group forms a ring structure of metallo-cyclopropene and its simple derivatives.

LDA and Sodium amide are the two most commonly used bases for the synthesis (generation) of 1-MCP (see U.S. Pat. No. 6,017,849). In the case of a sodium amide based reaction with allylic halide an elimination reaction is induced and forms sodio-cyclopropene, which is not stable and results in a quick release of 1-MCP gas (see F. Fisher and D. Applequist, *J. Org. Chem.*, 30, 2089 20 (1965)). In the case of LDA as reactant, a stabilized lithiation precursor of 1-MCP, lithio-cyclopropene, can be formed. This precursor requires addition of water to neutralize lithio-cyclopropene to generate 1-MCP. Both reaction processes can be relatively expensive and time consuming. Though LDA, as a reactant is relatively expensive and the storage of precursor requires controlled environment, which can further increase cost, the ability to store the precursor for an extended period, provides LDA based reactions an advantage over sodium amide.

Further, additional costs and significant safety concerns are raised due to 1-MCP and its analogs being relatively unstable. This instability is due to their reactive nature, particularly the potential for undergoing reactions, such as "ene" and/or oxidation. Due to the inherent volatility and reactivity of cyclopropene 2) compounds, they cannot be stored in the gaseous state for an extended period of time. Additionally, cyclopropene compounds, such as 1-MCP, is a gas under room temperature and is flammable, and thus poses a risk of explosion when compressed. Therefore, 1-MCP is often synthesized and then trapped into selective solid matrices for storage, handling, and application. The instability and the safety concerns for the 1-MCP gas can be addressed in various ways and have been addressed through various means, such as the encapsulating techniques disclosed in U.S. Pat. No. 6,017,849.

Both LDA and sodium amide based reactions for 1-MCP synthesis can result in the formation of and/or contamination with various impurities. Impurities refer to chemical substances that differ in composition and reduces the purity of the active ingredient, 1-MCP. Generally, the impurities are volatile or gaseous compounds that are formed from the reactants and the reaction, thus the impurities can include, without limitation, methylenecyclopropene, other cyclopropenes, butenes, and butanes. Unreacted reactants and various stabilizers also have potential to contaminate the 1-MCP gas. Generally, the contaminant impurities can include, without limitation, unreacted reactants such as 3-choro-2-methylpropene and stabilizers for lithium diisopropylamide such as heptane, ethylbenzene, hexane, and tetrahydrofuran. The impurities mix with the generated 1-MCP gas and travel with the gas stream through the process.

A synthesis reaction of 1-MCP can therefore be understood to have an impurity profile, comprising one or more impurities depending on the reactants used and reactions performed to synthesize 1-MCP. The impurity profiles for any specific synthesis reaction can be similar or significantly vary and be quite different. For instance, as shown in U.S. Pat. No. 6,953,540, if sodium amide is used to react with 3-CMP, the impurity profile can include unreacted 3-CMP, its isomer 1-chloro-2-methylpropene (1-CMP) and ammonia. Alternatively, if LDA is used to react with 3-CMP, the impurity profile can include unreacted 3-CMP, its isomer 1-CMP and volatile solvents used to stabilize LDA such as heptane, ethylbenzene, hexane, and tetrahydrofuran.

There are existing patents and methods to minimize the impurity level in 1-MCP. For example, U.S. Pat. No. 6,953,540 discloses a scrubbing system consisting of water to remove ammonia, and a reactive mixture comprising of a thiol, an alcohol, and an amine, to remove the unreacted 3-CMP. To reduce the level of unreacted 3-CMP, Chinese Patent No. 102167706 (CN 102167706) discloses a method of using vacuum distillation after forming lithio-cyclopropene. Similarly, Noeh et al. (2007) reported a method of using vacuum distillation to remove volatiles after synthesizing the lithio-cyclopropene.

All the aforementioned methods are effective for removing cyclopropene impurities, but have significant limitations that impact negatively on various synthesis and commercial factors. U.S. Pat. No. 6,953,540 disclosure is focused on sodium amide-based reactions and reactive methods for removing impurities. In the approaches disclosed by CN 102167706 and Noeh et al (2007), although vacuum distillation is effective to remove some impurities (volatiles), it may fail to meet EPA requirements, resulting in failed commercial outcomes, and may also not be efficient and cost-effective at an industrial level, thereby requiring significant capital investment and long processing time.

LDA based reactions result in a different impurity profile from the sodium amide reactions and therefore requires a different approach to minimize impurities. Controlling the impurity profile by eliminating, reducing and/or minimizing impurities evolved from the method of 1-MCP synthesis employed can significantly impact on various commercial factors and is critical in ensuring high purity and optimal loading of the pure 1-MCP gas into solid matrices for application and use. Thus, the methods (reactive or non-reactive processes) of removing impurities can also significantly impact upon the purification capabilities, purity of resulting compounds synthesized, reaction processes and costs involved. Further, controlling the impurity levels of the end product is a regulatory compliance matter enforced by the United States of America Environmental Protection Agency (US EPA). Impurity levels are strictly regulated by the US EPA, which requires 1-MCP impurity profiles to be below 0.1% of the total 1-MCP loading and the levels of chlorinated compounds 1-CMP and 3-CMP below 0.05% of total 1-MCP loading. Thus, significant commercial advantage and regulatory compliance can be realized through careful control over the impurity profile for any 1-MCP synthesis reaction and purification processes being employed.

It is therefore desirable to provide simple, physical (non-reactive) means and inert substances to purify 1-MCP gas generated from synthesis reactions, such as LDA based synthesis reactions, to ensure impurity profiles with eliminated, reduced and/or minimized impurity levels that satisfy certain regulatory compliance requirements and support commercial advantage.

SUMMARY OF THE INVENTION

In accordance with one aspect of the present invention, the foregoing and other objects are achieved in systems, methods and apparatuses that perform synthesis reactions, including a purification processing capability, preferably including at least one non-reactive purification means, for producing a purified 1-MCP gas ("P-1-MCP"). As such, any related analogs and precursors that are generated in the synthesis reactions may also comprise contemplated aspects of the present invention. The current invention significantly promotes the generation of a 1-MCP gas with an impurity profile that satisfies and/or exceeds various requirements, such as regulatory requirements regarding the presence or concentration of impurities and/or volatiles, also referred to herein as synthesis and/or reaction contaminants, found in a reaction product or compound. An impurity profile being an indication and measure (concentration) of the presence of unwanted organic, inorganic, residual solvents or any other unwanted chemicals, contaminants, volatiles and/or impurities that arise out of the generation, synthesis and/or purification of the 1-MCP gas. Still further, any of the systems, methods and apparatuses employed in a synthesis reaction of the current invention can also include and comprise one or more purification processing capabilities, including one or more non-reactive purification methods or processes, including any systems and apparatuses to support such purification processing capabilities.

In exemplary contemplated aspects consistent with embodiments of the current invention, a reaction system for the generation of 1-MCP gas can comprise, alone or in various combinations, integration and connection, one or more: (1) variously sized and functionally configured reaction vessels and/or devices which may also be referred to herein as reactors; (2) non-reactive purification systems; (3) various control mechanisms, for controlling the reaction and/or purification processes such as compound addition/removal, temperature, pressure, agitation (i.e., mixing), flow rate (gas and liquid compounds); and such other contemplated devices, mechanisms, and the like as may be contemplated by those skilled in the art. Still further, it is contemplated that additional functionalities, devices and mechanisms can be connected or integrated, alone or in any combination, as part of a reaction and/or non-reactive purification system including, without limitation, pump devices/mechanisms, distillation devices/mechanisms, regulators, and the like. The reaction vessels employed can be variously configured to provide a sealed or partially sealed reaction environment within which a reaction product or mixture can be generated and/or stored. Additionally, the systems of the current invention can allow other products/reactants or various chemical compounds to be added and for the removal of synthesis product(s), such as intermediates, precursors, and/or generated products.

Contemplated exemplary embodiments consistent with the invention can include methods for generating 1-MCP gas that include various purification systems (processing capabilities) that can employ, various processes, techniques and technologies, to remove unwanted contaminants, volatiles and/or impurities through various means including, without limitation, reactive and/or non-reactive means. The non-reactive means that may be employed by the current invention to remove impurities and volatiles, either alone or in various combinations, can comprise: (1) trapping and removing impurities in and using various non-reactive scrubbers or substances (referred to herein individually and collectively as "NRS", "NRS 1", "NRS 2", and the like) that can be individually employed, employed in various combinations and in varying numbers and amounts; (2) modifying reaction and non-reactive purification systems characteristics or conditions as are known and contemplated by those skilled in the art, such as temperature, pressure, gas flow rates, reaction time(s), contact surface area, scrubbing time; (3) physical pumping and removal of unwanted volatiles and impurities from the reaction systems: (4) vacuum distillation systems, such as (i) Still Pot Vacuum Distillation (SPVD), and (ii) Wiped Film (Column) Vacuum Distillation (WFVD) (iii) Falling Film Vacuum Distillation (FFVD), and (iv) Short-Path Vacuum Distillation (SPVD) and/or (5) such other methodologies, processes, techniques, technologies and the like as are contemplated by those skilled in the art that can provide for removal of impurities and volatiles in the generation of 1-MCP gas employing non-reactive means.

Contemplated purification processing systems and techniques that may be employed for any of the embodiments for the current invention can comprise one or in multiple combination(s), various purification capabilities and/or non-reactive substances or scrubbers (NRS). These purification capabilities can be applied to the 1-MCP gas generated during any phase of a 1-MCP synthesis in accordance with embodiments of the current invention, thereby removing in whole or part unwanted and potentially volatile contaminants and/or impurities from the products.

Non-reactive purification processes and techniques mean that impurities are removed through processes of solubilization, absorption, dissolution and/or other chemically non-reactive processes as opposed to chemical reaction between various chemicals and/or compounds. The non-reactive means employed by embodiments of the current invention may comprise addition to a synthesis process of one or more of inert or non-reactive materials or substances that do not significantly react with a gas stream containing a form of 1-MCP gas, such as unpurified 1-MCP (also referred to herein as "U-1-MCP"). The NRS include, but are not limited to, water, alcohol such as ethanol, methanol, and isopropanol; diol such as 1,3-propanediol and 1,2-propanediol; ketone such as acetone and butanone; haloalkane such as chloroform and carbon tetrachloride, mixtures of higher alkanes such as mineral oil; and benzene. More preferably, the non-reactive scrubber (NRS) mixture is selected from ethanol, acetone, 1,3-propanediol, and mineral oil. These chemicals are commercially available from suppliers such as Sigma Aldrich (Milwaukee, Wis.), Fisher Scientific (Hampton, N.H.), Shanghai Aladdin Bio-Chem Technology Co., LTD (Shanghai, China), and Optima Chemicals (Douglas, Calif.).

The current invention contemplates that the NRS can be a water-based solution, which can comprise 100% deionized water or a solvent-based solution comprising one diluted non-reactive solvent in water or a mixture of two or more non-reactive solvents in water. The volume percentage of non-reactive solvents ("scrubbers") in an NRS solution employed by the current invention can range from 10% to 100%, preferably from 30% to 80%, more preferably from 40% to 60%. Multiple NRS can be used to improve overall purification and promote achievement of desired impurity profiles. The number of NRS can range from 1 to 10, preferably from 1 to 8, more preferably from 1 to 5. One or multiple water-based or solvent-based NRS can be used following or prior to the use of one or more solvent-based or water-based NRS. It is contemplated that a water-based NRS may be used after use of a solvent-based NRS to remove water soluble impurities. Various water and solvent-based NRS solutions can be employed for the current invention, wherein the number of water-based NRS can range from 1 to 10, preferably from 1 to 8, more preferably from 1 to 5.

Contemplated exemplary embodiments of the current invention employ NRS containing mineral oil. It can be used alone or in conjunction with ethanol and acetone based scrubber. The viscosity of mineral oil also plays a role in the efficiency of purification. Preferably, the viscosity of mineral oil in this invention ranges from 2 to 350 $mm^2/s$ at 40° C., more preferably the viscosity range is from 3 to 310 $mm^2/s$ at 40° C. Multiple scrubbers containing mineral oil can be used. The number of solvent based NRS can range from 1 to 10, preferably from 1 to 8, more preferably from 1 to 5. Zero to multiple water based NRS can be used following the mineral oil scrubber to remove water soluble impurities. The number of water scrubbers can range from 1 to 10, preferably from 1 to 8, more preferably from 1 to 5.

In exemplary aspects contemplated by and for the current invention, a reaction system and method for generating a purified 1-MCP (P-1-MCP) gas employing the reaction system are provided. The reaction system and method can comprise a purification system that enables a non-reactive purification of an unpurified 1-MCP (U-1-MCP) gas stream by directly bubbling the gas stream through a non-reactive substance (NRS) in a vessel. Then the P-1-MCP can exit and/or be captured from the purification system via an outlet.

In additional exemplary aspects of the current invention, a reaction system and method for generating a purified 1-MCP (P-1-MCP) gas employing a reaction system are provided. The reaction system comprises a purification system that enables a non-reactive purification of an unpurified 1-MCP (U-1-MCP) gas stream by employing a co- or counter-current purification technique. This purification technique provides a method for purifying an U-1-MCP gas by flowing the U-1-MCP gas over a packed bed of materials including a non-reactive substance in a vessel. Then the P-1-MCP gas can exit and/or be captured from the purification system via an outlet.

In additional exemplary aspects of the current invention, a reaction system and method for generating a purified 1-MCP gas comprising a 1-MCP gas reactor functionally connected with a purification system is provided. The method comprises generating and releasing an unpurified 1-MCP (U-1-MCP) gas in a first reactor, and subjecting the purification systems to a vacuum pump that enables the released U-1-MCP gas to be flowed from the reactor into the purification system. The purification system comprises a first purification vessel including an NRS 1 and a second purification vessel including an NRS 2. The U-1-MCP gas is subject to multiple purification processing by flowing it through NRS 1 and then NRS 2 to generate a purified form of the 1-MCP gas. Then the purified 1-MCP gas can exit and/or be captured from the purification system via an outlet.

In still further contemplated exemplary aspects of the current invention, methods for generating a purified 1-MCP gas are provided. The methods can comprise generating an unpurified 1-MCP gas by reacting a precursor compound, formed from the reaction of an allyl compound with a strong base, with water. The unpurified 1-MCP gas can be subjected to a non-reactive purification processing capability, such as by bubbling and/or flowing the unpurified 1-MCP gas over or through a non-reactive substance or scrubber employing various techniques. From this non-reactive purification processing a purified 1-MCP gas is released. It is contemplated that the precursor compound can be subject to a first processing prior to its reaction with water, wherein the first processing may include a vacuum distillation processing or other processing as may be contemplated by those skilled in the art.

It is further contemplated for the exemplary aspects and embodiments of the current invention, that the purified 1-MCP gas generated can be encapsulated, wherein the purified form of the 1-MCP gas is encapsulated in a complex utilizing an alpha cyclodextrin (a-cyclodextrin). It is contemplated that various cyclodextrins, cyclodextrin polymers, mixtures and modified versions of such cyclodextrins can also be employed for the present invention.

The purification processing employed in the exemplary aspects and embodiments of the current invention can be employed in various combination(s), batch or continuous processing and at various scales. Still further, contemplated embodiments of the current invention can employ techniques, such as reusing or recycling of one or more of the NRS in a purification system. For example, an unpurified or purified 1-MCP gas stream can be processed or go through one or more NRS multiple times by directing the unpurified or purified 1-MCP gas back into an NRS for further purification. The NRS can also be reused in multiple production runs to improve the cost effectiveness of the production.

The preferred embodiments of this invention relate to reaction systems for providing a 1-MCP gas synthesis capability using various equipment at multiple scale for synthesizing various amounts of a 1-MCP gas. In the preferred embodiments, the reaction systems include a purification system(s) that can employ various purification processing capabilities. The purification capabilities can include gas scrubbing purification processes and others as contemplated by those skilled in the art.

BRIEF DESCRIPTION OF THE DRAWINGS

The objects and advantages of the invention will be understood by reading the following detailed description in conjunction with the drawings in which.

DETAILED DESCRIPTION

It should be emphasized that the terms "comprises" and "comprising", when used in this specification, are taken to specify the presence of stated features, integers, steps or components; but the use of these terms does not preclude the presence or addition of one or more other features, integers, steps, components or groups thereof.

Figure 1:
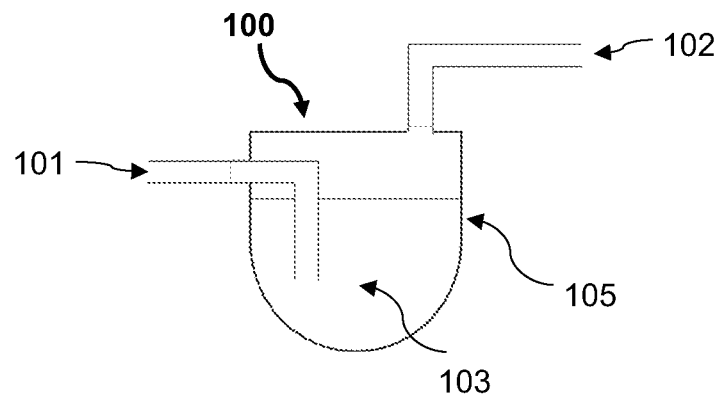
FIG. 1 is an illustration of a reaction system employing Non-Reactive Substances ("NRS") in which purification was achieved by direct bubbling U-1-MCP gas through non-reactive solution/solution mixture in accordance with the current invention.

Various configurations of systems that may be employed for the current invention and generate a purified 1-MCP gas are provided herein. In a preferred embodiment, as shown in FIG. 1, a system 100 promotes and can be employed to provide 1-MCP gas synthesis. The 1-MCP gas synthesis is accomplished in system 100 by directly bubbling a cyclopropene gas stream, such as an unpurified 1-methylcyclopropene gas stream, into a purification processing capability comprising an enclosed non-reactive scrubber, solvent-based (solvent/solvent) mixture shown as NRS 103 in FIG. 1. As shown in FIG. 1, a vessel 105, such as a sealed flask 105, can include or store the NRS 103. The NRS 103 is a mineral oil or other non-polar, non-reactive NRS compound (similar to and as may be referred to herein as "NRS 1") as contemplated. The sealed flask 105 is equipped with an inlet 101 that allows a compound, such as the gaseous compound of unpurified 1-methylcyclopropene (U-1-MCP) gas as identified above, to be added to the NRS 103 within the sealed flask 105. Sealed flask 105 further includes an outlet 102 which can allow the U-1-MCP gas that has been bubbled through NRS 103 to exit and potentially be captured. The gas compound captured from outlet 102 can be understood as a purified 1-methylcyclopropene (P-1-MCP) gas as identified above.

Figure 2:
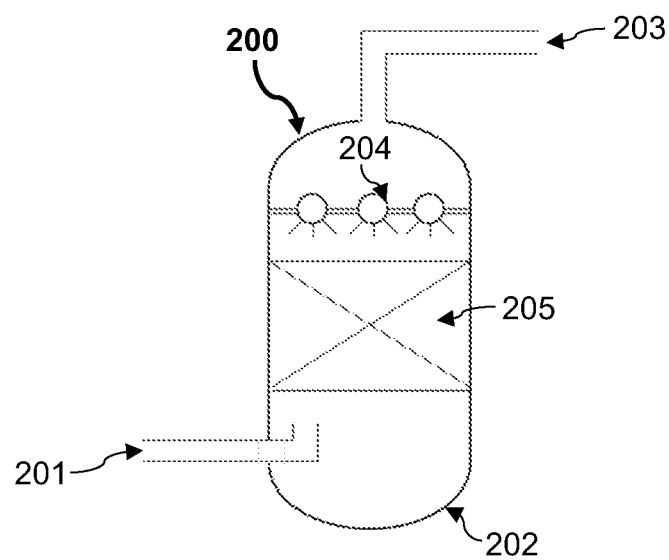
FIG. 2 is an illustration of a counter current purification system 200 in accordance with the current invention.

In addition, the synthesis of 1-MCP gas can also be accomplished in a system 200 employing or using a co- or counter flow non-reactive purification technique (scrubber). In the co- or counter flow scrubber, multiple layers of packing materials can be used as a packed bed. Packaging materials can include but not limited to Raschig rings, spiral rings, or Beri saddles, which can provide a large surface area for liquid-gas contact. The non-reactive purification system 200, as shown in FIG. 2, includes a purification vessel 202 configured with a counter-current gas scrubber functionality. In such an embodiment, a U-1-MCP gas (gas stream) may be fed through gas inlet 201 into a purification vessel chamber 202. An NRS, such as mineral oil or other non-polar and/or polar solvent(s), can be included in the purification vessel chamber 202. The mineral oil can be fed into the purification vessel 200 by being sprayed through spraying nozzle(s) 204. The spraying nozzle(s) 204 promote the distribution of the mineral oil (NRS) over a packed bed 205 within the purification vessel 202. Packed bed 205 is configured to promote sufficient and/or maximize the contact between the U-1-MCP gas stream and the NRS (mineral oil). Passage of the gas stream through packed bed 205 promotes the removal of contaminants and impurities (scrubbing of) from the U-1-MCP and generation of a purified 1-MCP (P-1-MCP) gas. The P-1-MCP gas can then exit the purification vessel 202 from outlet 203. This type of non-reactive purification (scrubbing) system 200, at various scales, can be commercially available from various suppliers.

Figure 3:
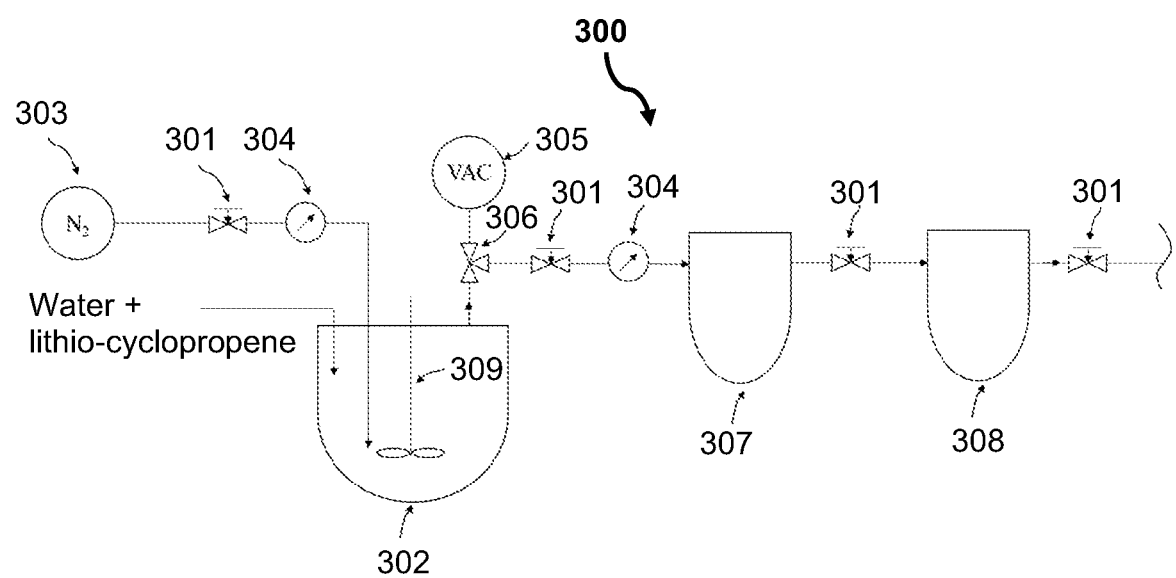
FIG. 3 is an illustration of a reaction and purification system 300 employed for the generation and purification of 1-MCP gas in accordance with the current invention.

An exemplary embodiment of a non-reactive purification system that can be employed as part of the current invention may include a non-reactive purification system 300 for generating a purified 1-MCP (P-1-MCP) gas as shown in FIG. 3. The system 300 includes a vacuum pump 305 controlled by a three-way valve 306 that is connected to reactor 302 first to remove air in the reactor. Then deionized water and lithio-cyclopropene (LCP) are added into reactor 302 to release a U-1-MCP gas. Nitrogen from tank 303 is introduced into the reactor and the flow rate of nitrogen gas ($N_2$) can be controlled by flow rate controlling valve 301 and flow rate meter 304. The reactor is agitated using an overhead stirrer 309. A vacuum pump 305 is then used to create vacuum in non-reactive purification vessels 307 and 308, to create the pressure difference between reactor 302 and the vessels 307 and 308. After adding lithio-cyclopropene and water, the three-way valve 306 is opened to introduce U-1-MCP and $N_2$ gas into the vessels 307 and 308. The purification processing provided by the current embodiment employs two NRS including a first NRS comprising 60% ethanol contained in vessel 307 and a second NRS comprising deionized water contained in vessel 308. The order of the two NRS employed can be altered by one skilled in the art.

A contemplated method of the current invention is exemplified by the following

Example 1: Generation of Li-1-MCP Precursor and Impurity Removal with Vacuum Distillation 1-MCP is generated by adding the allylic halide 3-choro-2-methylpropene (3-CMP) dropwise into lithium diisopropylamide (LDA) to form lithio-cyclopropene (referred to herein as "LCP" or "Li-1-MCP") which is the precursor to the 1-MCP gas. The LCP is then mixed with water, thereby promoting the removal of water soluble (polar) impurities in the LCP and the release of a 1-MCP gas. In general, the reaction scheme of 3-CMP and LDA for the synthesis of 1-MCP gas in accordance with the current invention can be illustrated as follows.

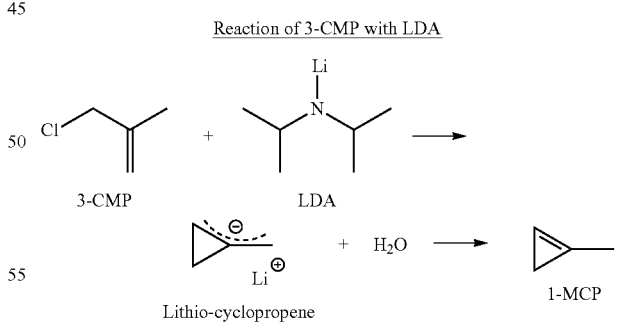

The allylic halide has a chemical structure of $H_2C=CH-CH_2X$, where "X" is the halogen (leaving) group, in this embodiment the chloride, which is eliminated during the reaction. R is a hydrogen or a substituted or unsubstituted alkyl, alkenyl, alkynyl, cycloalkyl, cycloalkylalkyl, phenyl, or naphthyl group improving the conversion rate of allylic halide into the LCP precursor compound. The conversion rate can be significantly promoted by employing an appropriate ratio of LDA to allylic halide. Preferably, the molar ratio of LDA to allylic halide is from 20:1 to 1:2. More preferably, the molar ratio is from 10:1 to 1:1. Most preferably, the molar ratio is from 5:1 to 1:1.

In the current example, the reaction between the allylic halide and the strong base LDA produces the lithio-cyclopropene precursor (LCP), which is a metallo-cyclopropene. It is contemplated for embodiments of the invention that the allyl compound can be various allylic compound with a sufficiently reactive structure that may comprise a leaving group and a reacting group. The allylic halides, such as an alkyl halide, includes one or more halogen atoms on the "allylic carbons" (the carbon atom next to a double bonded carbon atom). The role of these compounds can be as a metabolite, organic and inorganic chemicals which are the reactants, intermediates or products of enzyme-mediated biochemical reactions. These compounds are often identified as esters or salts with a zero net charge. In preferred embodiments, the halide employed may be 3-CMP, a methallyl chloride, 3-chloro-2-methylpropene, and the like as may be contemplated by those skilled in the art. Still further, other contemplated examples of allyl halides (salts) that can be employed with the current invention may include fluoride ion materials, such as fluoride salts in the form of alkyl or aryl ammonium salts and inorganic fluoride salts.

The current invention further contemplates the use of strong base compounds that can completely dissociate (ionize) in an aqueous solution. It is further contemplated that a strong base employed by the current invention be soluble in water and strongly non-nucleophilic. In embodiments, the base compound employed can comprise lithium diisopropylamide (LDA), phenyllithium, sodium amide or such other similarly strong bases. More particularly, the base compound employed in preferred embodiments of the current invention is the strong base LDA. The strong base employed can comprise a non-nucleophilic base with a $pK_a$ greater than 35. The non-nucleophilic bases employed can provide strong proton removing capability or functionality without any other functions, such as alkylation and complexation, which may negatively impact on the synthesis of the 1-MCP gas. It is contemplated that other similarly strong bases that can be employed by the current invention may include amides and/or hydrides, comprising silicon-based amides, such as sodium and potassium bis(trimethylsilyl) amide (NaHMDS and KHMDS, respectively), and/or sodium hydride (NaH) and potassium hydride (KH). The strong base compounds employed for the current invention may be dense, salt-like materials that are insoluble and operate in various manners, such as by surface reactions. Other contemplated suitable bases used for the method may include weak bases (<35 $pK_a$) or other strong bases (>35 $pK_a$) well-known in the art.

It is contemplated for this example 1 that the LCP solution can be suspended and stored in inert solvents such as a non-polar mineral oil, and then further be mixed with a polar substance like water to generate and release a 1-MCP gas. The impurities and contaminants in this process may include the solvents used to stabilize LDA such as ethylbenzene, heptane, tetrahydrofuran, hexane, and cyclohexane, as well as any unreacted 3-CMP which potentially isomerizes to 1-CMP during the process. These impurities have the potential to be trapped into the solid matrix and be present in the end product which can negatively impact upon the impurity profile and, therefore, the commercial viability and successful application of any 1-MCP gas.

In the current example 1, a reaction system can employ a reactor comprising a three-neck round-bottom flask. The three necks may be connected or integrated with various capabilities, such as adding or removing products from the flask and/or providing an agitation of the mixture in the flask. Therefore, the three neck flask can comprise: (1) a first compound control mechanism preferably comprising a dropwise addition capability, (2) an agitation control mechanism preferably comprising an overhead mechanical stirrer with a polytetrafluoroethylene (non-reactive) paddle, and (3) a second compound control mechanism preferably comprising a septa-closed syringe port for removing product from the flask. It is contemplated that one or more various compound and/or agitation control mechanisms as are known by those skilled in the art can be employed without departing from the scope and spirit of the current invention.

In the current example, the reactor is placed into an ice bath and the flask is flushed with nitrogen. It is contemplated that the reactor temperature can be optimized in a range from −40° C. to room temperature, or from −40° C. to 4C, and can be controlled using dry ice, ice, dry ice/acetone mixture, ice/acetone mixture and such other means as are known by those skilled in the art. A suspension of two (2M) moles of LDA in a solution that promotes the stabilization of the LDA was added into the flask under nitrogen flush. This LDA suspension or LDA solution can comprise a mix of the LDA and one or more various solvents, such as heptane, ethylbenzene, and tetrahydrofuran. Into this LDA suspension, 0.5 moles of the allylic halide 3-CMP is added in a dropwise manner. The reaction between the reactants, LDA and 3-CMP, generate the liquid LCP precursor. The solvents can further promote the reaction between the allylic halide and strong base and, thereby, the formation of the liquid LCP precursor. The sequence of adding the reactants may not necessarily promote a specific, desired increased efficiency in the reaction, but adding the base first, followed by the slow addition of the allyl compound is preferred and does appear to promote an efficient conversion and formation of the liquid LCP precursor.

In this preferred embodiment of example 1, the addition of the 3-CMP into the LDA solution in the flask is made dropwise at the rate of 1 mL/min, or a significantly similar approximate rate of addition, with the paddle or stirrer on at approximately 100 rpm. It is contemplated that the method, molarity, volume and rate of addition of the allylic halide employed by the current invention into the strong base solution within the flask can vary. For example, the 3-CMP can be added to the 2M LDA solution in the current example of the reaction vessel at a rate ranging from 0.1 m/min to 10 mL/min. After adding the 3-CMP into the LDA solution, this mixture was subjected to stirring by the paddle which was continued for another thirty (30) minutes. This reaction process resulting in the generation of LCP precursor. After this stirring process approximately 80% (v/v of LDA) of a light mineral oil was added into the reaction mixture forming a mineral oil/LCP mixture. Then the ice bath was removed. It is contemplated that the temperature of the flask (prior to and throughout the reaction process), duration of stirring by the paddle and rate (e.g., rpm of the paddle) of mixing employed, both during the addition of the 3-CMP and after a desired amount, concentration of 3-CMP in the reaction vessel has been achieved, can vary as contemplated by those skilled in the art.

The current invention contemplates the use of various non-reactive purification techniques to produce a 1-MCP gas with reduced levels of impurities. For the current example, the reaction mixture comprising the mineral oil/lithio-cyclopropene suspension (the LCP suspension) was subjected to a vacuum distillation system to at least partially remove impurities and volatiles generated from the formation of the LCP suspension from the reaction of LDA and 3-CMP. Two types of vacuum distillation systems were evaluated: (1) Still Pot Vacuum Distillation (SPVD), and (2) Wiped Film (Column) Vacuum Distillation (WFVD). Both vacuum distillation processes subjected the LCP suspension to distillation for a period of thirty (30) minutes. Throughout the distillation, the vacuum level was maintained at 26 in Hg to 30 in Hg. An amount of a final LCP suspension generated from the vacuum processing of the LCP suspension, particularly (0.2 mL), using the two methods was individually sampled. Each of the samples of the LCP suspension were then mixed in 2 mL of deionized water in a glass bottle equipped with a VICI valve and subjected to an agitation control mechanism, preferably a mechanical shaker. The mixing of the LCP suspension with the de-ionized water results in the release of 1-MCP gas from the mixture. This 1-MCP gas may also be understood and referred to herein as unpurified 1-methylcyclopropene (U-1-MCP) gas, wherein this form of the 1-MCP gas is also understood as an indication of a preliminary or initial form of the 1-MCP gas produced during the synthesis process. It is understood that this form of the 1-MCP gas can be generated prior to the application of a first non-reactive purification process in accordance with exemplary embodiments of the current invention. In the current example, after mixing of the LCP suspension and de-ionized water on a mechanical shaker for ten (10) minutes, headspace samples of the released 1-MCP gas were withdrawn using gas tight syringe and injected into GC-FID following CIPAC method 4667/m Detailed GC conditions are listed in Table 1. Results (Table 2) show that the vacuum distillation systems are effective to remove (scrub) volatile impurities and contaminants, and that the WFVD method was more efficient than the SPVD method in removing volatile impurities.

TABLE 1

GC condition

| | |
|---|---|
| GC type | Agilent 6890 |
| Column | DB-624 30 m length × 0.25 mm i.d. × 1.4 μm film thickness |
| Injection system | Injector mode: spilt injection<br>Injector insert: 4 mm i.d., straight through glass (no glass wool)<br>Injection volume: 0.50 mL |
| Split flow | 20 mL/min |
| Detector | Flame ionization |
| Temperature | Injection port: 75° C.<br>Detector: 185° C.<br>Oven program: temp 1, 40° C., hold 0 min, ramp rate 25° C./min; temp 2, 165° C., hold 1 min |
| Gas flow rates | Helium (carrier): 2 mL/min; approximately 40 cm/sec<br>Air: 400 mL/min<br>Hydrogen: 45 mL/min<br>Nitrogen (make up): carrier flow + make up flow = 30 mL/min |

TABLE 2

Results using different type of vacuum distillation method

| Method | 1-MCP purity (%) in the Li-1-MCP mineral oil suspension |
|---|---|
| No vacuum distillation | 16.4 |
| SPVD | 41.8 |
| WFVD | 73.2 |

Figure 4A:
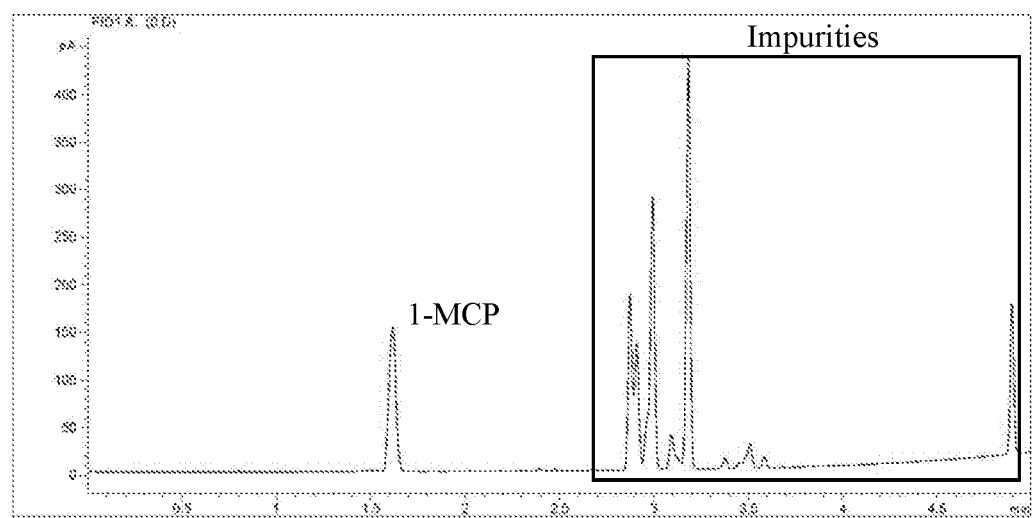
FIG. 4A is an illustration of the GC chromatogram of 1-MCP gas without vacuum distillation generated in accordance with the current invention.
Figure 4B:
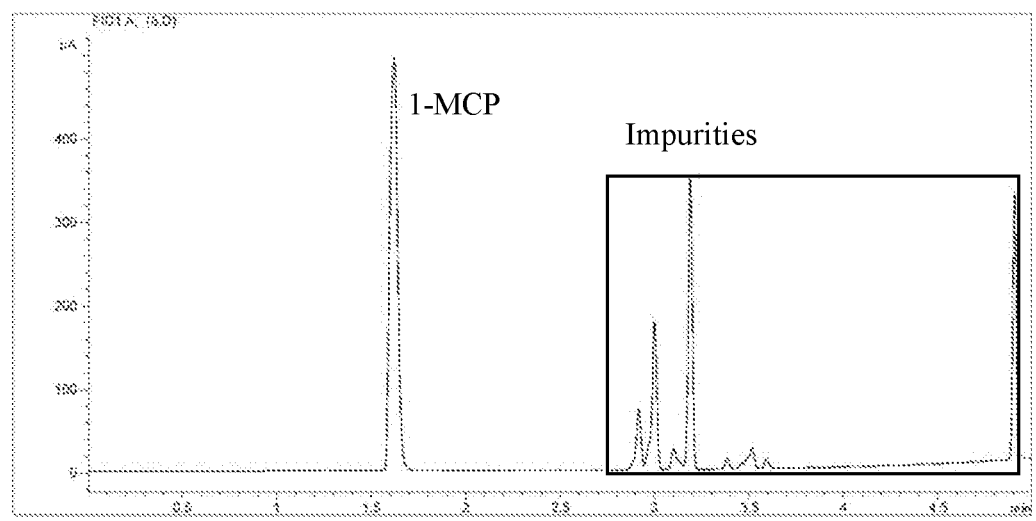
FIG. 4B is an illustration of the GC chromatogram of 1-MCP gas purified by using Still Pot Vacuum Distillation (SPVD) generated in accordance with the current invention.
Figure 4C:
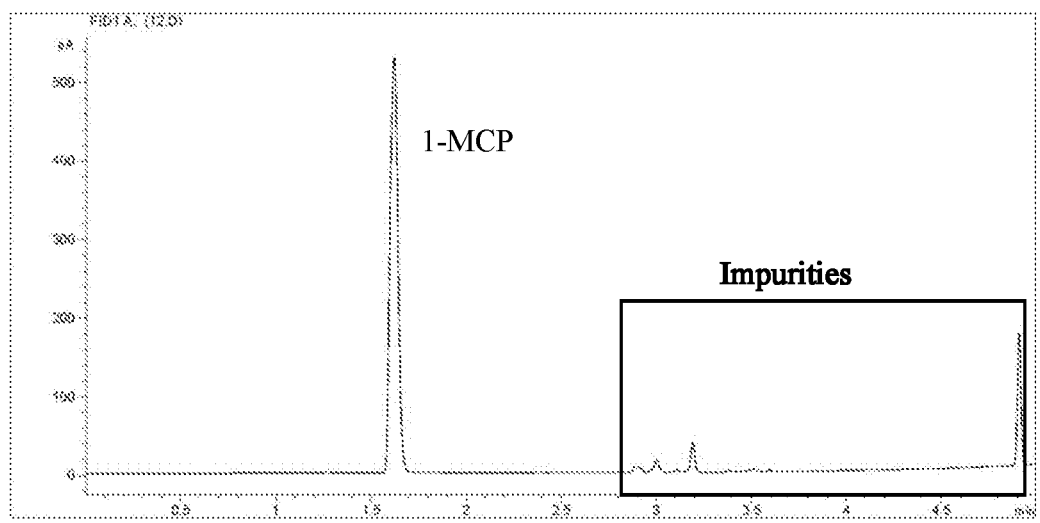
FIG. 4C is an illustration of the GC chromatogram of 1-MCP gas purified using Wiped Film Vacuum Distillation ("WFVD") generated in accordance with the current invention.

In the preferred embodiments shown in FIGS. 4A-4C (4A: GC chromatogram for U-1-MCP released from lithio-cyclopropene without vacuum distillation, 4B: GC chromatogram for 1-MCP by SPVD for 30 min, 4C: GC chromatogram for 1-MCP by WFVD), impurities were reduced in the order of no vacuum distillation>SPVD>WFVD. Percentage purity of 1-MCP is shown in Table 2.

Example 2: Addition of Water into Lithio-Cyclopropene (LCP) to Generate 1-MCP and Remove Water Soluble Impurities Lithio-cyclopropene (LCP), in the form of an LCP suspension, was prepared as shown in example 1 using the WFVD distillation technique. To test the effect of the amount of water on impurity level, 0.2 mL of the LCP suspension (lithio-cyclopropene/mineral oil suspension) was separately added into glass bottles containing various amounts of deionized water. The Oxygen atoms strongly attract electrons, and when freed from the water molecule, attracts the fairly positive lithium and separates or removes it from the cyclopropene. The glass bottles were equipped with VICI valves and were placed on a mechanical shaker for 30 minutes. Headspace, containing the 1-MCP gas, was sampled through the VICI valve and injected into GC-FID (same as Example 1). Table 3 shows that increasing the amount of water used in generation 1-MCP, its purity can be improved.

TABLE 3

Effect of water addition on impurity removal

| | 1-MCP purity |
|---|---|
| 0.2 mL lithio-cyclopropene in 150 mL deionized water | 85.7 |
| 0.2 mL lithio-cyclopropene in 100 mL deionized water | 86.5 |
| 0.2 mL lithio-cyclopropene in 50 mL deionized water | 81.6 |
| 0.2 mL lithio-cyclopropene in 20 mL deionized water | 81.4 |
| 0.2 mL lithio-cyclopropene in 2 mL deionized water | 73.2 |

Contemplated embodiments of the current invention include the addition of water to the LCP, in its various forms, not only to generate 1-MCP, but also as a non-reactive scrubber to trap water soluble impurities that may be present in the LCP solution, including without limitation tetrahydrofuran (THF). The ratio of water to LCP in embodiments of the current invention can range from 500:1 to 1:2, preferably from 100:1 to 1:1, more preferably from 50:1 to 1:1.

In contemplated embodiments, a polar solvent such as water can be the NRS employed, which solubilizes and removes water soluble impurities from the precursor compound (LCP suspension). Various other NRS compounds and substances, such as those described below in example 3, including other polar and/or non-polar solvents, can be used with the contemplated methods of the current invention and as contemplated by those skilled in the art. The non-reactive NRS interaction with the precursor compound can promote the evolution of an unpurified and/or purified 1-MCP gas.

Example 3: Purification Efficiency of Different NRSs

Lithio-cyclopropene (LCP) was prepared as shown in example 1 using the WFVD purification technique. The WFVD purification process was extended to 1 hour by slowing down the flow rate of the LCP suspension (LCP/light mineral oil) through the wiped film column, resulting in a 1-MCP gas with 91% purity. It can be understood for the current invention that this form of the 1-MCP gas, and any form of the 1-MCP gas produced by the current invention, an be an unpurified (U-1-MCP) or purified (P-1-MCP) form. Around fifteen (15) mL of lithio-cyclopropene was added into two hundred (200) mL deionized water in a six hundred (600) mL generation vessel under agitation and nitrogen flush. The generation vessel was connected to NRS(s) through a nylon tube by directly bubbling the gas into the NRS(s). As described below, the NRS(s) employed for this example include de-ionized water, mineral oil and ethanol, in various combination and order of application. Each NRS was incubated in a refrigerator for thirty (30) minutes before use. Headspace sample was collected through septum equipped on the NRS and subjected to GC analysis (similar to that described for example 1). The quantification of identified potential impurities were conducted using each impurity compound (>99% purity) as an external standard for GC measurement and calculation. Composition of NRS and purification efficiency are shown in the Table 4 and indicate that NRS 3-5 were most effective in removing the identified impurities and promotes the synthesis of a purified 1-MCP (P-1-MCP) gas that meets or achieves EPA specified purity requirements.

TABLE 4

Effect of different NRSs on impurity removal

| NRS # | Purification system composition | Identified impurities and concentration (%) in 1-MCP | | | | |
|---|---|---|---|---|---|---|
| | | 3-CMP | 1-CMP | Heptane | Ethylbenzene | THF |
| 1 | Without NRS | ND* | ND | 3.9 | 14.3 | 0.8 |
| 2 | NRS: DI water | ND | ND | 5 | 2 | ND |
| 3** | NRS-1: mineral oil NRS-2: DI water | ND | ND | 0.06 | ND | ND |
| 4** | NRS: 50% ethanol | ND | ND | 0.05 | ND | ND |
| 5** | NRS-1: 50% Ethanol NRS-2: DI water | ND | ND | 0.08 | ND | ND |

*ND: not detected
**Reached EPA specified purity level

Example 4: Mineral Oil as NRS for Impurity Removal

1-MCP was generated, vacuum distillation and purification was applied using the method shown in example 3. Four different types of mineral oil with different viscosities were used as the NRS. In each test, only one NRS was used. Headspace sample was collected through a septum equipped on the NRS, and subjected to GC analysis (same as example 1). The quantification of identified potential impurities were conducted using each impurity compound (>99% purity) as external standard for GC measurement and calculation. Purification efficiency is shown in Table 5 below. Results show that Blandol® (Sonneborn®, Petrolia, Pa.) and Hydrobrite® 550 (Sonneborn®, Petrolia, Pa.) were able to reduce all impurities under the EPA specified impurity level, while Hydrobrite® 1000 (Sonneborn®, Petrolia, Pa.) and Hydrobrite® HV (Sonneborn®, Petrolia, Pa.) did not. Multiple Hydrobrite® 1000 and Hydrobrite® HV may be needed to achieve the same purification efficiency as Blandol® and Hydrobrite® 550.

TABLE 5

Effect of different mineral oil on impurity removal

| NRS | Identified impurities and concentration (%) in 1-MCP | | | | |
|---|---|---|---|---|---|
| | 3-CMP | 1-CMP | Heptane | Ethylbenzene | THF |
| Without scrubber | ND | ND | 3.9 | 14.3 | 0.8 |
| Hydrobrite® 1000$ | ND | ND | 0.39 | 0.26 | ND |
| Blandol® *,$ | ND | ND | 0.07 | ND | ND |
| Hydrobrite® 550$ | ND | ND | 0.09 | 0.09 | ND |
| Hydrobrite® HV$ | ND | ND | 0.37 | 0.27 | ND |

* Same as Scrubber 3 in Example 3.
$Reached EPA specified purity level

Example 5: Effect of Number of NRS

1-MCP was generated, vacuum distillation and purification was applied using the method shown in example 3. Blandol® mineral oil was used as NRS. One-NRS, two-NRS, and three-NRS reaction system protocols were tested. Headspace sample was collected through a septum equipped on the NRS, and subjected to GC analysis (same as example 1). The quantification of identified potential impurities were conducted using each impurity compound (>99% purity) as external standard for GC measurement and calculation. The results are shown in the Table 6. Results show that by increasing the number of NRS employed during a purification process for the 1-MCP gas, the impurity levels can be further reduced.

TABLE 6

Effect of number of scrubber on impurity removal

| Mineral oil | Identified impurities and concentration (%) in 1-MCP | | | | |
|---|---|---|---|---|---|
| | 3-CMP | 1-CMP | Heptane | Ethylbenzene | THF |
| Without scrubber | ND | ND | 3.9 | 14.3 | 0.8 |
| One-NRS* | ND | ND | 0.07 | ND | ND |
| Two-NRS* | ND | ND | 0.06 | ND | ND |
| Three-NRS* | ND | ND | 0.04 | ND | ND |

*Reached EPA specified purity level

Example 6: Purified 1-MCP from α-Cyclodextrin Encapsulation Complex

1-MCP was generated, vacuum distillation and purification was applied using the method shown in example 3. NRS 5 in example 3 was used to purify 1-MCP gas. Encapsulation was conducted based on Neoh, T. L., et al., "Kinetics of Molecular Encapsulation of 1-Methylcyclopropene into α-Cyclodextrin". Journal of Agricultural and Food Chemistry, 2007. 55(26): p. 11020-11026. Encapsulation using U-1-MCP was also conducted as control. The resulted encapsulation complex was dissolved in deionized water in a glass bottle equipped with VICI valve. The glass bottle was placed on a mechanical shaker for 30 min and headspace was sampled for GC analysis (same as example 1). The quantification of identified potential impurities were conducted using each impurity compound (>99% purity) as external standard for GC measurement and calculation. The resulted chromatogram is shown in FIG. 5. Table 7 shows that no 1-CMP or 3-CMP was detected in both cases, but more impurities were detected in samples prepared using U-1-MCP. In samples prepared using P-1-MCP, no impurity more than 0.1% of 1-MCP was detected, reaching the EPA specified purity level.

TABLE 7

1-MCP released from encapsulation complex

| | Identified impurities and concentration (%) in 1-MCP | | | | |
|---|---|---|---|---|---|
| | 3-CMP | 1-CMP | Heptane | Ethyl-benzene | THF |
| Encapsulated using U-1-MCP | ND | ND | 0.66 | 1.41 | 0.32 |
| Encapsulated using P-1-MCP* | ND | ND | 0.06 | ND | ND |

*Reached EPA specified purity level

Figure 5A:
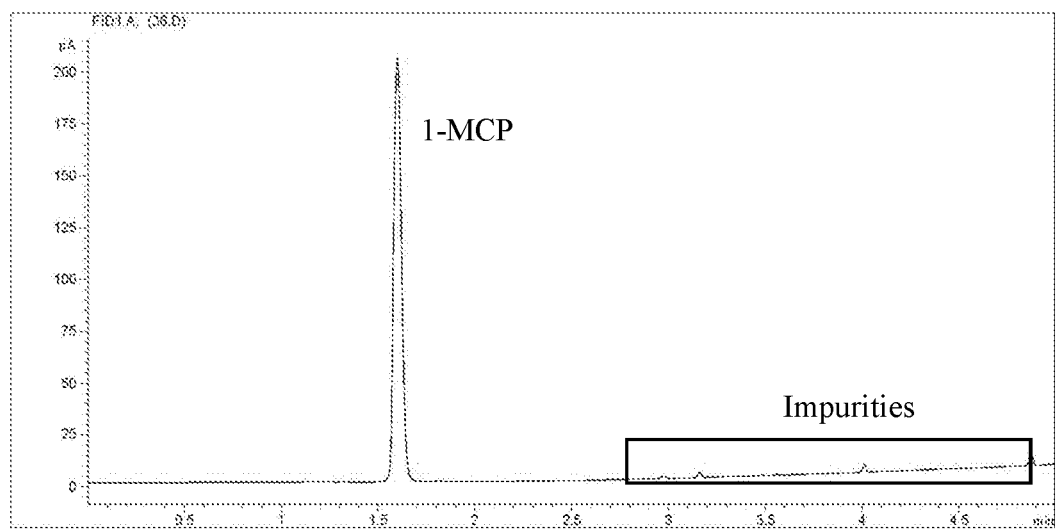
FIG. 5A is an illustration of GC chromatogram of 1-MCP released from encapsulation complex prepared using U-1-MCP.
Figure 5B:
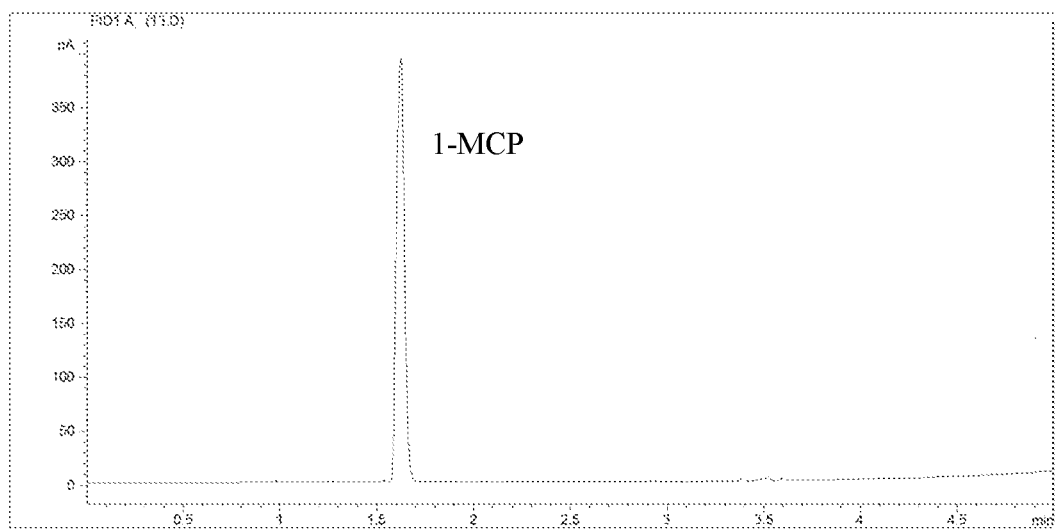
FIG. 5B is an illustration of GC chromatogram of 1-MCP released from encapsulation complex prepared using P-1-MCP.

In the preferred embodiments shown in FIGS. 5A-5B (5A: GC chromatogram for 1-MCP released from a-cyclodextrin containing U-1-MCP, 5B: GC chromatogram for 1-MCP released from a-cyclodextrin containing P-1-MCP), purification method specified in Example 6 is efficient in promoting the removal of impurities and the 1-MCP released from the final product can have high purity level which meet or exceed EPA regulatory requirements.

Example 7: Re-Use of NRS

1-MCP was generated, vacuum distillation and purification was applied using the method shown in example 3. NRS 5 in example 3 was used to purify 1-MCP gas for 3 times. Between each use, vacuum (26 in Hg to 30 in Hg) was applied to the NRS and was incubated in refrigerator for 30 min. Headspace sample was collected through a septum equipped on the reactor, and subjected to GC analysis (same as example 1). The quantification of identified potential impurities were conducted using each impurity compound (>99% purity) as external standard for GC measurement and calculation. Results are shown in the Table 8. Similar purification results were obtained for each use of the scrubbing system, and the 1-MCP purity level reached EPA specification.

TABLE 8

Effect of re-using the purification solution on impurity removal

| | Identified impurities and concentration (%) in 1-MCP | | | | |
|---|---|---|---|---|---|
| | 3-CMP | 1-CMP | Heptane | Ethyl-benzene | THF |
| 1$^{st}$ use* | ND | ND | 0.08 | ND | ND |
| 2$^{nd}$ use* | ND | ND | 0.07 | ND | ND |
| 3$^{rd}$ use* | ND | ND | 0.09 | ND | ND |

*Reached EPA specified purity level

Example 8: Effect of Temperature of NRS on Impurity Removal

1-MCP was generated, vacuum distillation and purification was applied using the method shown in example 3. NRS 5 in example 3 was used to purify 1-MCP gas. NRS incubated in dry ice bath for 30 min and NRS kept under room temperature were compared. Headspace sample was collected through a septum equipped on the NRS, and subjected to GC analysis (same as example 1). The quantification of identified potential impurities were conducted using each impurity compound (>99% purity) as external standard for GC measurement and calculation. Results are shown in the Table 9. Although both processes resulted in 1-MCP purity level reaching EPA limits, NRS incubated in dry ice had less impurity level than NRS at room temperature.

TABLE 9

Effect of NRS temperature on impurity removal

| | Identified impurities and concentration (%) in 1-MCP | | | | |
|---|---|---|---|---|---|
| | 3-CMP | 1-CMP | Heptane | Ethyl-benzene | THF |
| NRS incubated in dry ice* | ND | ND | 0.05 | ND | ND |
| NRS kept at room temperature* | ND | ND | 0.09 | 0.05 | ND |

*Reached EPA specified purity level

For contemplated exemplary embodiments of this invention, 1-MCP synthesis means, without limitation, method(s) for the synthesis, including purification processing, of a purified 1-MCP (P-1-MCP) gas. The purified 1-MCP gas synthesized can be encapsulated in a-cyclodextrin for stabilization and storage, as explained in example 6.

In an embodiment consistent with the invention, a method for generating a purified 1-methylcyclopropene (P-1-MCP) gas in a purification system similar to that shown in FIG. 1 is provided. This method comprises mixing an LCP solution with water in a reactor thereby forming a reaction mixture within the reactor. The mixing results in the release of an unpurified form of a 1-methylcyclopropene (U-1-MCP) gas. The released U-1-MCP is then subjected to a purification processing, in this embodiment this is a non-reactive purification (scrubbing) process whereby the U-1-MCP is directly bubbled through a solution containing at least one non-reactive substance or scrubber (NRS). The NRS can be a polar or non-polar, water-based or solvent-based solution providing a scrubbing of the U-1-MCP, the scrubbing being a non-reactive means for the removal of at least some contaminants, impurities and/or volatiles present in the released U-1-MCP. From the scrubbing of the U-1-MCP with the at least one NRS a final, purified form of a 1-MCP gas (P-1-MCP) is released. The P-1-MCP gas can be captured from the NRS, such as through an outlet in the NRS similar to that shown in FIG. 1. It is contemplated that the P-1-MCP gas may be encapsulated in a-cyclodextrin for stabilization, storage and additional processing, as explained above in example 6 and contemplated by those skilled in the art.

In an additional embodiment consistent with the invention, a method for generating a purified 1-methylcyclopropene (P-1-MCP) gas in a purification system similar to that shown in FIG. 2, wherein a purification system is configured with a counter-current gas scrubber functionality, is provided. This method comprises mixing an LCP solution with water in a reactor thereby forming a reaction mixture within the reactor. The mixing results in the release of an unpurified 1-methylcyclopropene (U-1-MCP) gas. The released U-1-MCP is then subjected to a purification processing, in this embodiment this is a non-reactive purification (scrubbing) process whereby the U-1-MCP is flowed through a co- or counter-current purification system configuration similar to that shown in FIG. 2. In the co- or counter flow scrubber, multiple layers of packing materials can be used as a packed bed. The packed bed is configured to promote sufficient and/or maximize the contact between the U-1-MCP gas stream and the NRS. Packaging materials can include but not limited to Raschig rings, spiral rings, or Beri saddles, which can provide a large surface area for liquid-gas contact. An NRS solution containing at least one polar and/or non-polar, non-reactive substance or scrubber is employed. The NRS can be a water-based or solvent-based solution providing a scrubbing of the U-1-MCP, the scrubbing being a non-reactive means for the removal of at least some impurities and/or volatiles present in the released U-1-MCP. In the current embodiment, the NRS is a mineral oil (solvent-based solution) and it is contemplated that other non-polar and/or polar solvent(s) can be included without departing from the scope and spirit of the current invention. The mineral oil can be fed into the purification system by being sprayed through spraying nozzle(s) or other distribution control means. The spraying nozzle(s) can promote the distribution of the mineral oil (NRS) over the packed bed within the purification vessel. From the scrubbing of the U-1-MCP with the at least one NRS a final, purified form of 1-MCP (P-1-MCP) gas is released. The P-1-MCP gas can exit the purification system and/or be captured from the purification system, such as through an outlet in the purification vessel similar to that shown in FIG. 2. It is contemplated that the P-1-MCP gas may be encapsulated in a-cyclodextrin for stabilization, storage and additional processing, as explained above in example 6 and contemplated by those skilled in the art.

In an embodiment consistent with the invention, a method for generating a purified 1-methylcyclopropene (P-1-MCP) gas is provided. It is contemplated that this method can be performed in a reaction and purification system similar to the reaction and purification system 300 as shown in FIG. 3. This method comprises generating a lithio-cyclopropene (LCP), which is the precursor formed during a synthesis reaction of 1-MCP gas. The LCP is generated and provided in suspension or solution (LCP solution). The LCP solution is then mixed with water forming a reaction mixture, whereby the mixing results in the release of an unpurified form of a 1-methylcyclopropene (U-1-MCP) gas. The released U-1-MCP is then subjected to a non-reactive purification (scrubbing) process whereby the U-1-MCP is mixed with at least one polar and/or non-polar non-reactive substance or scrubber (NRS). The NRS providing a scrubbing of the U-1-MCP, the scrubbing being a non-reactive means for the removal of at least some impurities and/or volatiles present in the released U-1-MCP. From the scrubbing of the U-1-MCP with the at least one NRS a final, purified form of a 1-MCP (P-1-MCP) gas is released. It is contemplated that the P-1-MCP gas may be encapsulated in a-cyclodextrin for stabilization, storage and additional processing, as explained above in example 6 and contemplated by those skilled in the art.

Figure 6:
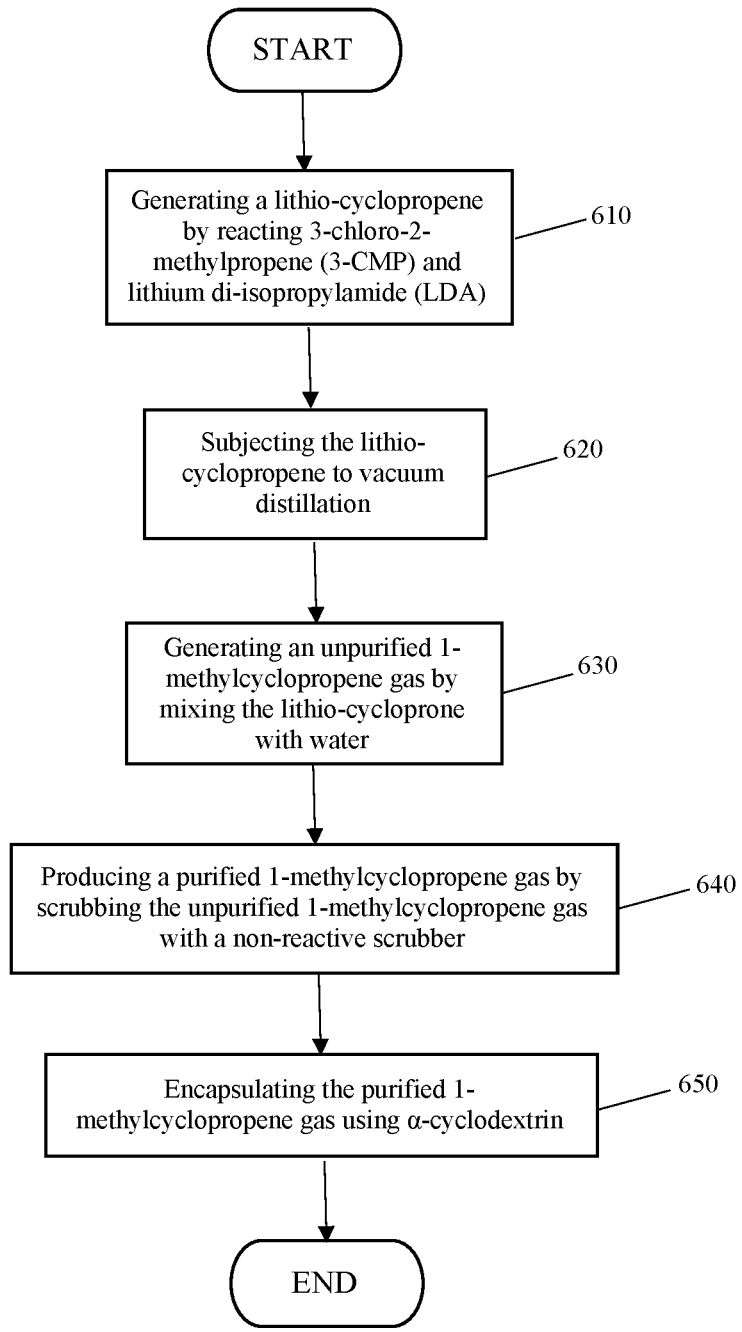
FIG. 6 is a block diagram illustrating a method for generating 1-MCP gas in accordance with an exemplary embodiment of the current invention.

In another embodiment consistent with the invention shown in FIG. 6, a method 600 for generating a purified 1-methylcyclopropene (P-1-MCP) gas is provided. This method comprises a step 610 for generating a lithio-cyclopropene (LCP), which is the precursor formed during a synthesis reaction of 1-MCP gas. The LCP being generated and provided in suspension or solution (LCP solution). The LCP solution, in step 620 is then subjected to a vacuum distillation processing for promoting removal of at least some contaminants and impurities that may be present in the LCP solution to obtain a higher concentration of LCP in the solution. After the distillation processing, in step 630, the LCP solution is then mixed with water forming a reaction mixture, whereby the mixing results in the release of an unpurified form of 1-methylcyclopropene (U-1-MCP) gas. The released U-1-MCP is then subjected to a scrubbing process in step 640, whereby the U-1-MCP is mixed with at least one polar and/or non-polar, non-reactive substance or scrubber (NRS). The NRS providing a scrubbing of the U-1-MCP, the scrubbing being a non-reactive means for the removal of at least some contaminants, impurities and/or volatiles present in the released U-1-MCP. From the scrubbing of the U-1-MCP with the at least one NRS in step 640, a final, purified form of a P-1-MCP gas is released. It is contemplated that the P-1-MCP gas may be encapsulated in a-cyclodextrin for stabilization, storage and additional processing, as explained above in example 6 and contemplated by those skilled in the art.

For the exemplary embodiments, including as indicated for step 610 of method 600, generation of the LCP precursor can be accomplished in various manners. For a preferred embodiment, it can comprise contacting an allyl compound with a non-nucleophilic strong base, such as a sodium amide or lithium amide. It is further contemplated, for the preferred embodiment of method 600, that the allyl compound can be an allylic halide compound, such as 3-chloro-2-methylpropene (3-CMP), and the strong base can be lithium diisopropylamide (LDA).

The synthesis reaction for forming LCP is accomplished by adding the allylic halide, 3-chloro-2-methylpropene (3-CMP), dropwise into a lithium diisopropylamide (LDA) solution. The interaction of 3-CMP and LDA is promulgated in a reaction vessel, such as a flask or other contemplated device. This synthesis reaction typically occurs in a suspension or solution environment, which is referred to herein as the "LDA solution" or "LDA suspension". The LDA solution can comprise the LDA, which is a strong non-nucleophilic base, and one or more non-polar, non-reactive solvents used to stabilize the LDA, such as heptane, ethylbenzene, tetrahydrofuran (THF) and other solvents as may be contemplated by those skilled in the art. It is contemplated that prior to or contemporaneously with the addition of the LDA solution and/or the dropwise addition of the allyl halide 3-CMP the reaction vessel can be subject to a nitrogen flush. The nitrogen flush being a protection agent that promotes the optimization of the reaction, by promoting that the reaction of the allyl compound and strong base takes place under inert condition.

The reaction between the allylic halide and the LDA produces the lithio-cyclopropene (LCP) precursor, which is a metallo-cyclopropene, in solution. The LCP is suspended in the initial LDA solution within which the reaction of the LDA and 3-CMP takes place. In the preferred embodiment of method 600, an inert mineral oil is added and suspends the LCP. The LCP suspended in the LDA solution and also when suspended in the mineral oil solution (referred to herein as the "LCP solution" or "LCP suspension") can be the precursor used to generate and release 1-MCP gas. The properties and/or characteristics of such an LCP solution can vary and range as contemplated by those skilled in the art. It is further contemplated for exemplary embodiments that the LCP solution can be further suspended and stored in various inert solvents and/or solutions as may be contemplated by those skilled in the art.

The presence of contaminants and impurities in the LCP solution can impact upon the purity of any 1-MCP gas that may be evolved therefrom. The contaminants and impurities that may be generated from the method(s) of the current invention and present in this LCP solution can include, without limitation, the solvents used to stabilize LDA in solution, such as ethylbenzene, heptane, tetrahydrofuran (THF), hexane, and cyclohexane, as well as any unreacted 3-CMP which potentially isomerizes to 1-CMP during the LCP synthesis reaction process. These contaminants and impurities have the potential to be trapped into the solid matrix and be present in any released 1-MCP gas.

In method 600, the LCP solution generated in step 610 is subjected to a vacuum distillation processing in step 620 for promoting removal of at least some impurities that may be present in the LCP solution and providing an increased or higher concentration of LCP in the LCP solution. The vacuum distillation system processing provided in step 620 for the current embodiment may preferably include the WFVD technique (as described herein), but may also include other techniques such as the SPVD. It is contemplated that the WFVD processing may promote the generation of an LCP solution with a higher concentration of LCP thereby promoting an increased availability of LCP for generation and release of 1-MCP gas.

It is contemplated for exemplary embodiments of the current invention that prior to a generation and release of 1-MCP gas from any precursor solution, including the LCP solution of method 600, the application of an initial processing, such as may be provided by employing a vacuum distillation system and which can be understood as an aspect of the non-reactive purification capabilities of the current invention, can be employed. In various contemplated embodiments consistent with the current invention, one or more of the various vacuum distillation techniques and technologies as described herein can be employed to promote the removal of impurities from one or more suspensions, solutions, mixtures and the like. For instance, vacuum distillation techniques, such as (i) Still Pot Vacuum Distillation (SPVD), and (ii) Wiped Film (Column) Vacuum Distillation (WFVD) can be employed to provide a purification of the LCP solution. The vacuum can be achieved using a vacuum pump connected to the reactor or reaction vessel (i.e., flask and the like) through a condenser with a cold water jacket or filled with dry ice to a still pot, hereafter referred to as still pot vacuum distillation ("SPVD"). It can also be a more sophisticated system such as a wiped film distillation system ("WFVD") in which a rotating blade is employed to create a very thin and turbulent film of LCP, or a falling film vacuum distillation ("FFVD") in which the LCP is falling downwards along a tube to create a thin film on the tube walls, or a short-path vacuum distillation ("SPVD") in which LDP travels from one chamber to another chamber through a short path. The vacuum level provided by the vacuum distillation systems employed by the current invention can range from 5 to 30 in Hg, preferably is 10 to 30 in Hg.

Impurity and contaminant removal from any mixture, such as the LCP solution, can promote a solution containing a higher concentration of reactant, such as LCP, and/or with a decreased or lower percentage of impurities. This can also promote an increase or improvement in the reaction potential of a reactant in a solution. For exemplary embodiments of the current invention, this can promote an increased availability of LCP to ultimately synthesize 1-MCP gas from the LCP solution. It is contemplated that these exemplary purification processing techniques can promote a precursor solution, such as the LCP solution, with an increased efficiency and effectiveness in achieving the release of 1-MCP gas. For instance, the LCP solution generated after application of the WFVD processing in the preferred embodiment of method 600, may have an increased efficiency and effectiveness in generating 1-MCP gas as compared to that of an LCP solution that is not subjected to an exemplary purification processing as contemplated by the current invention. Thus, it is further contemplated that increased efficiency and effectiveness in generating 1-MCP gas may be accomplished using one or more various purification systems, that may employ one or more different purification processes, techniques and technologies, as is contemplated by the current invention. The method(s) for generating such a purified precursor during 1-MCP synthesis, including the LCP solution or such other precursor(s) as are contemplated by those skilled in the art, can be understood as an embodiment(s) of the current invention, as a separate reaction methodology and process or as incorporated into and/or integrated with the 1-MCP synthesis.

After the distillation processing, in step 620, the LCP solution, as indicated for exemplary embodiments of the current invention including in step 630, is then mixed with water forming a reaction mixture. The reaction mixture promotes a reaction between the LCP and water resulting in the generation and release of a 1-MCP gas. This form of the 1-MCP gas may be understood and referred to herein as a preliminary and/or unpurified 1-methylcyclopropene (U-1-MCP) gas. This form of the 1-MCP gas can be an example of a preliminary or initial form of the 1-MCP gas produced during the synthesis process and prior to the generation of a final form of the 1-MCP gas. It is contemplated for this method that after removing impurities from the LCP solution using a vacuum distillation technique (such as the WFVD employed), a polar substance, such as water, is added to the LCP solution to react with the LCP to generate a form of 1-MCP gas by removing the lithium ion from the LCP. The water addition can also remove some polar impurities in the LCP solution, including without limitation THF. The ratio of water to the LCP solution in embodiments of the current invention can range from 500:1 to 1:2, preferably from 100:1 to 1:1, more preferably from 50:1 to 1:1.

In a first instance, the form of unpurified-1-MCP (U-1-MCP) gas, can be understood as a preliminary form of 1-MCP gas generated prior to the application of a purification processing technique. In other contemplated examples and embodiments, various preliminary forms of a 1-MCP gas can be generated, wherein these preliminary forms of the gas can be produced after being subjected to one or more purification processing techniques contemplated by the current invention. For example, where a 1-MCP gas is subjected to multiple purification processing techniques it may be understood that the form(s) of the 1-MCP gas generated from each purification processing applied is a preliminary form. In this manner, the U-1-MCP form of the 1-MCP gas is understood as one or more preliminary forms of the gas that may be generated prior to a final, purified form of the 1-MCP gas being generated in accordance with exemplary embodiments of the current invention.

For the exemplary embodiments, including as indicated for step 640 of method 600, the released U-1-MCP is then subjected to a non-reactive purification process (scrubbing), whereby the U-1-MCP is mixed with at least one non-reactive substance or scrubber (NRS). The scrubbing being a non-reactive purification processing technique or means that promotes and provides for the removal of at least some impurities and/or volatiles, also referred to herein as contaminants, synthesis and/or reaction contaminants, present in the released U-1-MCP via non-reactive means. In step 640 of the preferred embodiment of method 600, and for various other contemplated embodiments of the current invention, the NRS solution contains a mixture of non-reactive solvents, including alcohol, diol, and ketone. It is contemplated that the NRS solution can be water-based or dilute solvent-based without departing from the scope and spirit of the current invention. From the scrubbing of the U-1-MCP with the at least one NRS, a final, purified form P-1-MCP gas is produced and released. It is contemplated that the weight percentage of individual impurity in the P-1-MCP gas ranges from 0.001 to 10%, 0.005 to 5%, and less than or equal to 0.1%. It is contemplated that the generated and released U-1-MCP gas can be subjected to various non-reactive purification techniques and technologies in accordance with embodiments of the invention and additional contemplated embodiments consistent with the invention. For the exemplary embodiments, including as indicated for step 650 the purified 1-MCP gas is encapsulated in a-cyclodextrin for stabilization, storage and additional processing, as explained above in example 6 and contemplated by those skilled in the ant. The weight percentage of individual impurity in 1-methylcyclopropene gas generated from the encapsulation complex of the P-1-MCP gas and a-cyclodextrin, in any of the embodiments and examples presented herein for the current invention, may range from 0.001 to 10% or 0.005 to 5%, more preferably 0.1% or lower.

The contaminants and impurities present for any exemplary embodiments of the current invention including, without limitation, as may be found in any of the solutions, mixtures, intermediates, precursors and/or synthesized (generated) gases and products (also referred to herein collectively as the "compounds"), establishes an impurity profile for the compound(s) and can negatively impact upon the application and use of any of the various compounds. Impurity profiles which identify the amount of any impurities present in a compound that do not satisfy various regulatory requirements may prohibit the continued use and application of those compounds, significantly restrict the application and use of those compounds and/or require additional processing to achieve regulatory compliance. The current invention, through use of its purification processing in any exemplary embodiments, such as purified 1-MCP synthesis, promotes the avoidance of these types of outcomes which may negatively impact on commercial success of the compounds, for instance by increasing production time and costs.

It is contemplated by the current invention that the level, amount and/or concentration of contaminants and impurities that may be present in any compound prior to the application of any purification systems and processes may significantly vary. The application of a purification processing, as may be contemplated by the current invention, during any phase of 1-MCP synthesis can significantly impact on the impurity profile for any compound(s). It is contemplated that after the application of a purification processing, either as a single processing or in combination with any of the other various purification processing techniques, the individual impurity percentage in 1-MCP can range from 0 to 10%, 0.005 to 5%, more preferably less than or equal to 0.1%. It is contemplated that the purification processing of the current invention can be applied individually or in various combinations to accomplish a desired impurity profile for any compound as may be found and/or generated during a contemplated 1-MCP synthesis for the current invention.

Promoting the efficiency and effectiveness of any purification process employed for the current invention can be accomplished through various means and mechanisms, including temperature and gas flow rate control, and as are further contemplated by those skilled in the art. Temperature control mechanisms for the 1-MCP synthesis, either partially or entirely, are contemplated. From the above example, in step 620, the reactor's connection to the vacuum pump through a condenser with a cold water jacket or filled with dry ice is an exemplary temperature control mechanism that can be employed with the current invention. This temperature control mechanism can promote a temperature range between −40° C. to room temperature, more preferably from −40° C. to 4° C. The temperature can be controlled using dry ice, ice, dry ice/acetone mixture, and ice/acetone mixture. Lower temperature of the NRS helps lower the volatility of the impurities in U-1-MCP, thereby helps trapping them better in the NRS system. Various different and/or additional temperature control mechanisms can be employed with the exemplary embodiments of the current invention.

Flow rate control mechanisms for controlling a flow rate either for a solution (i.e., LCP solution, reaction mixture, and the like) or a gas (i.e., unpurified 1-MCP and/or purified 1-MCP, and the like) are contemplated. Depending on the throughput and production rate, various flow rates can be used. If a relatively fast rate is used, then the residence time of the solution or gas, such as U-1-MCP or P-1-MCP gas, in the non-reactive solvent is short and thus two or more NRS may be needed. If a relatively slower rate is used, then the residence time of the solution or gas, such as U-1-MCP or P-1-MCP gas, is longer and provide more contact of the solution or gas with the non-reactive solvent and thus one or two NRS may be sufficient. For the above example, LCP solution or reaction mixture is or can be charged into the non-reactive purification vacuum distillation system using a metering pump at specific flow rates ranges from 1 mL/min to 60 mL/min, preferably from 5 mL/min to 50 mL/min, more preferably from 10 mL/min to 40 mL/min. People with ordinary skill related to the art can calculate the desired flow rate based on the throughput required from the process.

Other contemplated purification techniques and systems that may be employed for any of the embodiments for the current invention can comprise the addition of multiple, various non-reactive substances or scrubbers (NRS) to any products, such as the LCP solution, reaction mixture or any form (purified or unpurified) of the 1-MCP gas generated, thereby removing unwanted and potentially volatile impurities from the products.

As described, a purified LCP solution can ultimately promote the release of various forms of a 1-methylcyclopropene (1-MCP) gas, including unpurified and purified, in accordance with the methods of the current invention, which can further promote a desired impurity profile for the 1-MCP gas. A desired impurity profile for a 1-MCP gas is one that satisfies and/or exceeds particular regulatory requirements regarding the concentrations of various impurities present in the 1-MCP gas. Failure to satisfy regulatory requirements can result in a 1-MCP gas that is commercially unacceptable and unusable which can result in increased costs and significant delays in production. By synthesizing a purified LCP solution the current invention can significantly promote the regulatory and commercial expectations of success for synthesis of a 1-MCP gas that meets or exceeds impurity profile regulatory requirements.

It is further contemplated that method embodiments for generating a 1-MCP gas by utilizing a precursor compound(s) can employ other non-reactive purification techniques, such as employing a pump mechanism for drawing off unwanted solvents in the precursor solution, such as the LCP solution. For instance, prior to the addition of mineral oil into the LCP solution and vacuum distillation as described in method 600 above, some residual solvents in LCP can be physically pumped out of the reactor. This can result in a purified or more highly concentrated LCP solution and may promote shorter processing times for additional purification systems, such as the vacuum distillation system and/or other non-reactive purification techniques. This pump process may be further optimized by conducting it after an amount of the precursor, such as the LCP, settles in the synthesis reactor, but can be performed at various stages of the reaction process as contemplated by those skilled in the art.

The methods and systems described in above embodiments can be combined and used selectively by people with ordinary skill related to the art, based on the needs of production and resources available. The invention has been described with reference to particular embodiments. However, it will be readily apparent to those skilled in the art that it is possible to embody the invention in specific forms other than those of the embodiment described above. The described embodiments are merely illustrative and should not be considered restrictive in any way. The scope of the invention is given by the appended claims, rather than the preceding description, and all variations and equivalents which fall within the range of the claims are intended to be embraced therein.

What is claimed is:

1. A method of preparing a purified cyclopropene gas, comprising:
   producing a treated lithium-based precursor of 1-methylcyclopropene gas by subjecting a lithium-based precursor of 1-methylcyclopropene gas to a vacuum distillation system to at least partially remove impurities and/or volatiles;
   reacting the treated lithium-based precursor of 1-methylcyclopropene gas with water to generate an unpurified 1-methylcyclopropene gas; and
   producing a purified 1-methylcyclopropene gas by scrubbing the unpurified 1-methylcyclopropene gas with at least one non-reactive scrubber, wherein the non-reactive scrubber is a polar or non-polar compound, and at least partially removes synthesis and/or reaction contaminants from the generated unpurified 1-methylcyclopropene gas,
   wherein the purified 1-methylcyclopropene gas has regulatory compliance impurity presence of less than 0.1 wt. % for each of the synthesis and/or reaction contaminants.

2. The method of claim 1, further comprising synthesizing the lithium-based precursor by reacting an allyl compound with a non-nucleophilic strong base, wherein a molar ratio of allylic halide to strong base is from 20:1, to 10:1, to 5:1, to 1:1 to 1:2.

3. The method of claim 1, wherein the lithium-based precursor is a lithio-cyclopropene and a volume ratio of water to the lithio-cyclopropene ranges from 500:1 to 1:2.

4. The method of claim 1, wherein the lithium-based precursor is suspended in a mineral oil having a viscosity range from 2 to 350 mm²/s at 40° C., or from 3 to 310 mm²/s at 40° C.

5. The method of claim 1, wherein the non-reactive scrubber is at least one of a water and/or a solvent-based mixture, and a total number of non-reactive scrubbers employed ranges from 1 to 10, 1 to 8 or 1 to 5.

6. The method of claim 1, further forming an encapsulation complex comprising the purified 1-methylcyclopropene gas utilizing an α-cyclodextrin.

7. The method of claim 6, wherein a percentage of individual impurity in a 1-methylcyclopropene gas generated from the encapsulation complex of the purified 1-methylcyclopropene gas and α-cyclodextrin is 0.1 wt. % or lower.

8. The method of claim 1, wherein a percentage of individual impurity in the purified 1-methylcyclopropene gas ranges from 0.1 wt. % to 0.001 wt. %, or j less than or equal to 0.001 wt. %.

9. The method of claim 1, wherein a temperature range for the scrubbing performed with the non-reactive scrubber ranges from −40° C. to room temperature.

10. The method of claim 1, wherein the non-reactive scrubber comprises at least one of a water, alcohol, diol, ketone, haloalkane, carbon tetrachloride, mixtures of higher alkanes, and/or benzene.

11. The method of claim 1, wherein the non-reactive scrubber contains one or more polar solvents in water at a concentration ranging from 10 to 100 vol. %, 30 to 80 vol. %, or 40 to 60 vol. %.

12. The method of claim 1, further comprising subjecting the lithium-based precursor to a pump that physically removes at least some of the reaction contaminants.

13. The method of claim 1, wherein the vacuum distillation system has (i) a vacuum level that ranges from 5 to 30 inch Hg or 10 to 30 inch Hg and (ii) a flow rate of the lithium-based precursor charged into the vacuum distillation system ranges from 1 ml/min to 60 ml/min, from 5 ml/min to 50 ml/min or from 10 ml/min to 40 ml/min.

14. The method of claim 1, wherein the purified 1-methylcyclopropene gas is recycled through the non-reactive scrubber.

15. The method of claim 1, wherein the unpurified 1-methylcyclopropene gas is directly bubbled through the non-reactive scrubber.

16. The method of claim 1, wherein the unpurified 1-methylcyclopropene gas is subjected to a second non-reactive scrubber after being scrubbed with the non-reactive scrubber.

17. The method of claim 1, wherein the purified 1-methylcyclopropene gas is subjected to a non-reactive scrubber.

18. The method of claim 1, wherein the regulatory compliance impurity comprises 1-chloro-2-methylpropene (1-CMP) and 3-chloro-2-methylpropene (3-CMP).

19. A method of preparing a purified cyclopropene gas, comprising:
   synthesizing a purified 1-methylcyclopropene gas by reacting a treated lithium-based precursor of 1-methylcyclopropene gas with water to generate an unpurified 1-methylcyclopropene gas, wherein the treated lithium-based precursor is generated by subjecting a lithium-based precursor of 1-methylcyclopropene gas to a vacuum distillation system to at least partially remove impurities and/or volatiles, and scrubbing the unpurified 1-methylcyclopropene gas with at least one non-reactive scrubber, wherein the non-reactive scrubber is a polar or non-polar compound, and at least partially removes at least one synthesis and/or reaction contaminants from the generated unpurified 1-methylcyclopropene gas,
   wherein the purified 1-methylcyclopropene gas has 1-chloro-2-methylpropene (1-CMP) and 3-chloro-2-methylpropene (3-CMP) each present in an amount of less than 0.1 wt. %.

20. The method of claim 19, further forming an encapsulation complex comprising the purified 1-methylcyclopropene gas utilizing an α-cyclodextrin.

* * * * *